United States Patent [19]

Rho et al.

[11] Patent Number: 5,108,746
[45] Date of Patent: Apr. 28, 1992

[54] STABILIZER COMPOSITION AND STABILIZED AQUEOUS SYSTEMS

[75] Inventors: Jinnque Rho, Orange; Peter J. Ghirla, Stamford, both of Conn.

[73] Assignee: Daleco/Protech Partners, L.P., Newport Beach, Calif.

[21] Appl. No.: 346,474

[22] Filed: May 2, 1989

Related U.S. Application Data

[63] Continuation-in-part of Ser. No. 209,516, Jun. 21, 1988, abandoned, and a continuation-in-part of Ser. No. 194,489, May 16, 1988, abandoned.

[51] Int. Cl.$^5$ .............................................. A61K 37/62
[52] U.S. Cl. ................................ 424/94.2; 424/94.3; 424/76.6; 424/76.8; 424/76.9; 514/386; 514/398; 514/404; 514/407
[58] Field of Search .................... 424/76.6, 76.8, 76.9, 424/94.2, 94.3; 514/386, 398, 404, 407

[56] References Cited

U.S. PATENT DOCUMENTS 4,115,546  9/1978  Vidra et al. ............................ 424/50

FOREIGN PATENT DOCUMENTS 8402058  6/1984  PCT Int'l Appl. .

OTHER PUBLICATIONS

Llabres et al. Appl. Env. Micro. 49(2):370–373 (1985).
Rosen et al. J. Soc. Cosmet Chem. 24:663–675 (1973).
Becrens et al. CA94(13):96957 (1981).
Berke et al. J. Soc. Cosmet. Chem. 29:757–766 (1978).

*Primary Examiner*—Douglas W. Robinson
*Assistant Examiner*—Jean C. Witz
*Attorney, Agent, or Firm*—Christie, Parker & Hale

[57] ABSTRACT

Stabilizer compositions for use in stabilizing aqueous systems, especially aqueous based enzyme compositions, comprise an alkali metal salt of an aromatic carboxylic acid and a potentiating amount of a methylolated urea possessing a heterocyclic ureido substituent.

13 Claims, No Drawings

STABILIZER COMPOSITION AND STABILIZED AQUEOUS SYSTEMS

RELATED APPLICATIONS

This application is a continuation-in-part of our prior copending application Ser. No. 07/209,516, filed Jun. 21, 1988, now abandoned, and a continuation-in-part of our prior application Ser. No. 194,489, filed May 16, 1988, now abandoned.

FIELD OF THE INVENTION

This invention relates to improved stabilizer compositions for stabilizing aqueous systems, especially aqueous based enzyme compositions against bacterial contamination and to aqueous based systems stabilized against bacterial contamination.

BACKGROUND OF THE INVENTION

Water based compositions for a wide variety of purposes are well known, such as for example, aqueous based compositions useful as shampoos, cleansing creams, cosmetics, eye preparations, body lotions, pharmaceuticals, physiological saline solutions, odor and stain eradicators, disinfectants, suppositories and the like. The production of such compositions is such that it is intended that bacterial contamination be eliminated by killing of the bacteria during processing and production of the product. However, because of the adaptability of bacteria, particularly Pseudomonas bacteria, and because its nutritional demands are modest, it can survive and multiply quite easily. This is especially true with water based enzyme compositions where problems with the presence and growth of gram positive and gram negative bacteria severely limit the stability period of shelf life of the compositions to a period of about three to four months.

It has been discovered that the aforedescribed microbial contamination problem is especially prevalent in water based enzyme containing products due to contamination and growth of *Pseudomonas aeruginosa*. As a result of the aforesaid microbial contamination problem in water based enzyme containing products the marketing and use of such products has been inhibited.

Moreover, the presence and growth of bacterial contamination in the various types of water based products described hereinbefore can present a health hazard to those who utilize such products and incur the risk of bacterial infection. Severe health problems can result to those who utilize such contaminated products and are especially susceptible to contracting bacterial infections, such as chronically ill or severely debilitated persons and those on antibiotics or immunosuppressive therapy.

While stabilizers against such bacterial contaminations have heretofore been proposed, such stabilizers have not been particularly satisfactory or of sufficient efficacy to produce products of relatively long-term stability. Since the aforementioned compositions are often utilized in a manner that they require contact with skin or mucous membranes of humans or animals, it is necessary to utilize stabilizers or preservatives that are nontoxic, free or substantially free of harmful side effects and are environmentally safe to humans and animals. However, such stabilizers which have the aforesaid desirable characteristics have not been able to provide sufficient effective stabilization to water based compositions to enable the products to be stable over extended periods of time and during constant use.

It is therefore highly desirable that such water based compositions be stabilized so that the risk of bacterial infection from such products be eliminated or substantially eliminated and that such products have an increased shelf life or stability. It is also desirable that water based enzyme compositions be stabilized against bacterial contamination to produce water based enzyme compositions having a shelf life or stability of about two years or more and that such stabilized compositions be environmentally acceptable and safe to humans and animals who are exposed to or contact such compositions.

SUMMARY OF THE INVENTION

It has been discovered that aqueous based compositions of greatly improved stability with respect to bacterial contamination can be obtained by the addition thereto of a synergistic stabilizing amount of a. a water soluble salt of a carboxylic acid, and
b. a potentiating amount of an alkylolated urea possessing a heterocyclic ureido substituent, or
c. the interaction product of a. and b.

The invention embraces a concentrate aqueous composition suitable for use in aqueous solutions subject to bacterial contamination composition comprising a mixture of or the interaction product of a. a water soluble salt of a carboxylic acid, and
b. a potentiating amount of an alkylolated urea possessing a heterocyclic ureido substituent.

The invention includes an aqueous based compositions of greatly improved stability with respect to bacterial contamination obtained by the addition thereto of a synergistic stabilizing amount of a. an alkali metal salt of a carboxylic acid, and
b. a potentiating amount of a methylolated urea possessing a heterocyclic ureido substituent of the formula:

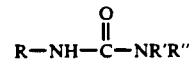

wherein each of R and R" may be one of hydrogen, alkyl (preferably lower alkyl, such as alkyl containing 1-4 carbon atoms), hydroxyalkyl (preferably lower alkyl, such as alkyl containing 1-4 carbon atoms), and alkoxyalkyl (preferably lower alkyl in each case, such as alkyl containing 1-4 carbon atoms), or R', and R' may be a heterocyclic group of the formula:

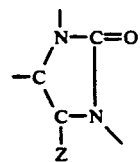

wherein one of the free valences thereof is bonded to the nitrogen of the urea, and the remaining free valences are bonded to one of hydrogen, alkyl (preferably lower alkyl, such as alkyl containing 1-4 carbon atoms), hydroxyalkyl (preferably lower alkyl, such as alkyl containing 1-4 carbon atoms), and alkoxyalkyl (preferably lower alkyl in each case, such as alkyl containing 1-4 carbon atoms), Z satisfies the free valence of the carbon atom to which it is bonded and may be oxo(=O), hydrogen, hydroxyalkyl, alkyl, monovalent heterocyclic radicals containing a ring bonded

where the free valences of the nitrogen are saturated, and the like moieties, and x is a number equal to the free valence of the carbon atom to which Z is bonded.

In a preferred embodiment of the invention, the invention relates to aqueous based compositions of greatly improved stability with respect to bacterial contamination obtained by the addition thereto of a synergistic stabilizing amount of
 a. an alkali metal salt of an aromatic carboxylic acid and
 b. a potentiating amount of a methylolated urea possessing a heterocyclic ureido substituent.

The invention also embraces stabilizer compositions for use in stabilizing aqueous systems, especially aqueous based enzyme compositions, which comprise an alkali metal salt of an aromatic carboxylic acid and a potentiating amount of a methylolated urea possessing a heterocyclic ureido substituent.

In the most preferred embodiment, the invention relates to aqueous based compositions of greatly improved stability with respect to bacterial contamination containing a synergistic stabilizing amount of
 a. and alkali metal salt of benzoic acid and
 b. diazolidinyl urea of the formula

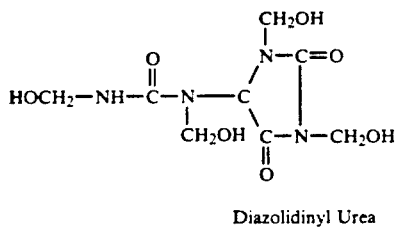

Diazolidinyl Urea and/or an imidazolidinyl urea of the formula

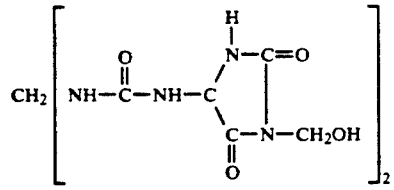

Imidiazolidinyl Urea

DETAILED DESCRIPTION OF THE INVENTION

This invention is concerned with the stabilization of systems useful against such bacterial contaminations. More particularly, the invention relates the stabilization of aqueous compositions for a wide variety of purposes, such as for example, aqueous based compositions useful as shampoos, cleansing creams, cosmetics, eye preparations, body lotions, pharmaceuticals, physiological saline solutions, odor and stain eradicators, disinfectants, suppositories and the like. This invention overcomes difficulties inherent in prior art systems which purport to provide stability from bacterial contamination. Coupled with the problem of stabilization is the fact that useful compositions are often utilized in a manner that they require contact with skin or mucous membranes of humans or animals, and this invention addresses that by providing a stabilizer system that has been established as nontoxic, free or substantially free of harmful side effects and environmentally safe to humans and animals.

The stabilizer system of the invention utilizes:
 i. a water soluble salt of a carboxylic acid, and
 ii. a potentiating amount of an alkylolated urea possessing a heterocyclic ureido substituent, or
 iii. the interaction product of i. and ii.

The term "interaction product," as used herein and in the claims, means the association of i. and ii. by molecular attraction ranging from strong to weak bonding relationships, including without limitation, covalent bonding, ionic bonding, Van der Waal forces, hydrogen bonding and/or associative bonding.

The water soluble salt of a carboxylic acid includes those carboxylic acids that posses inhibitive effects toward bacterial contamination. An attribute of the acid is that in the salt-free form, it is not normally soluble in water, or is essentially water insoluble. For example, the invention would not be realized from the use of esters and acids, per se, that are water insoluble because they are incapable of synergistically interacting with component ii. above. Though the invention contemplates the use of the stabilizer system in aqueous emulsions that possess a water phase and an oil phase, the stabilizer system of the invention is designed for use in the water phase and consequently, it should possess the requisite solubility in that phase.

Illustrative of suitable water soluble salts are water soluble salts of organic carboxylic acids, such as water soluble salts of organic carboxylic acids that are normally not water soluble. Desirable water insoluble acids are the aromatic caboxylic acids such as those of the formulae:

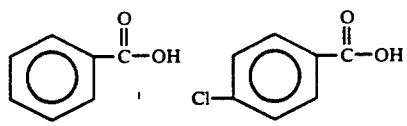

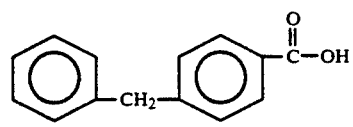

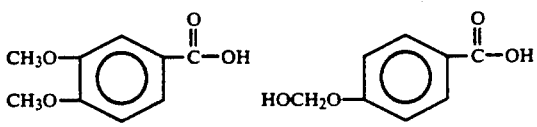

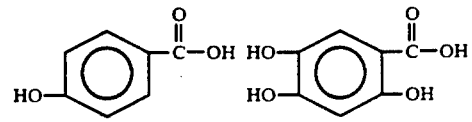

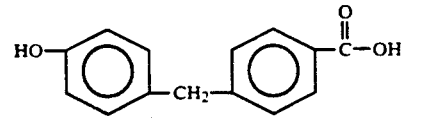
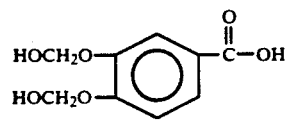
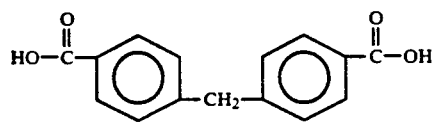
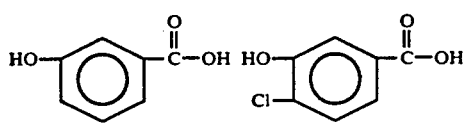
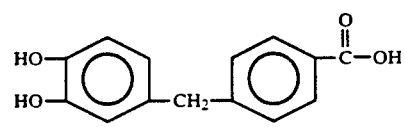
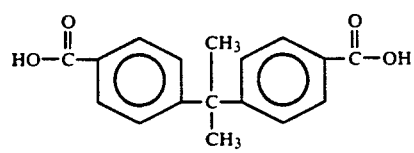
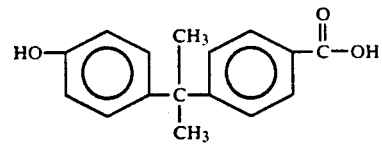
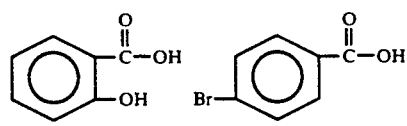
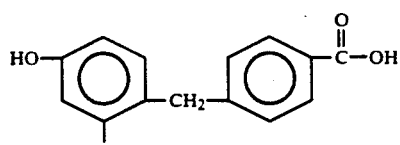
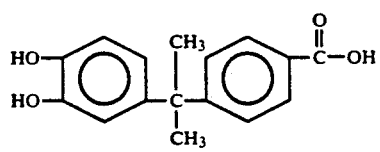
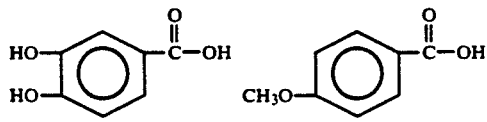
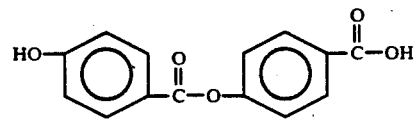

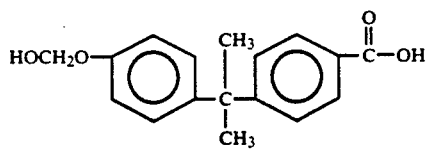

The salt forming component suitable in solubilizing the aforementioned acids and providing the advantages of the invention include the alkali metal salts, the quarternary ammonium salts, and the like. Suitable salt forming cations include

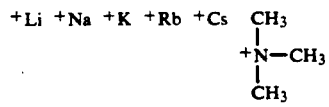
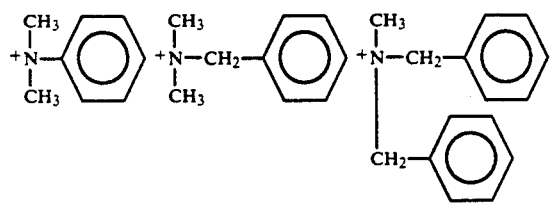
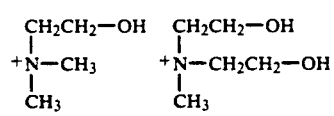
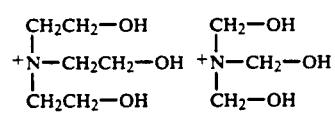

The alkylolated urea are water soluble compounds that possess a heterocyclic ureido substituent and include the following:

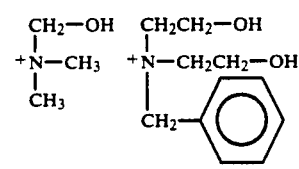

wherein each of R, R' and R" are as defined above.

That category of materials includes alkylolated ureas of the following structures:

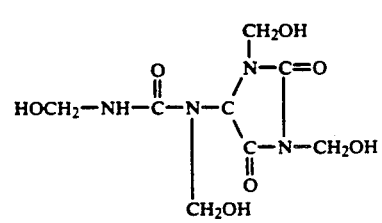

-continued

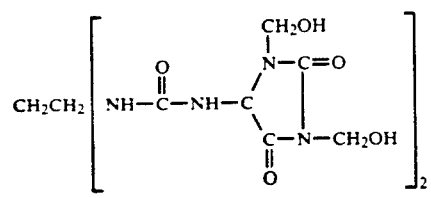

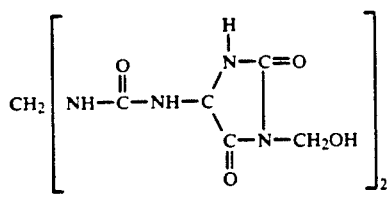

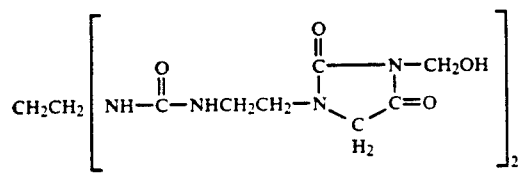

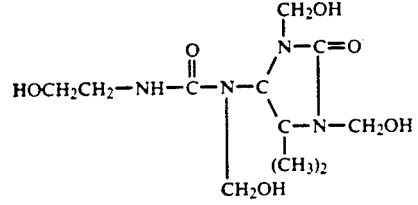

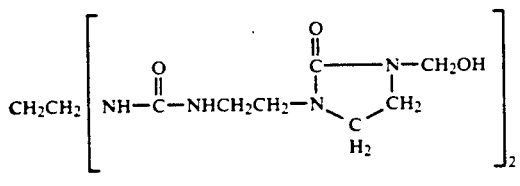

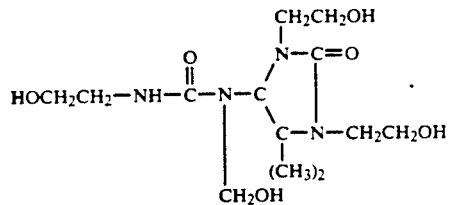

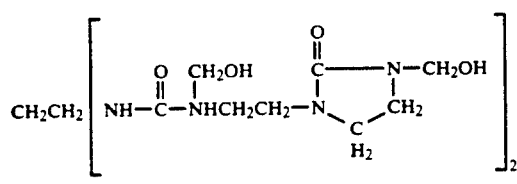

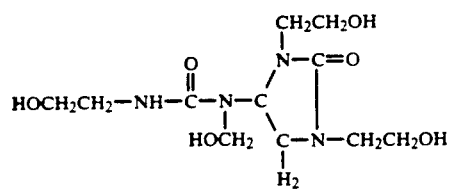

The most preferred compositions of the invention encompass aqueous based compositions of greatly improved stability with respect to bacterial contamination containing a synergistic stabilizing amount of a. and alkali metal salt of benzoic acid and
b. diazolidinyl urea of the formula

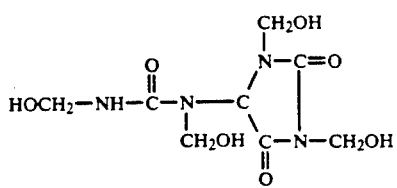

Diazolidinyl Urea and/or an imidazolidinyl urea of the formula

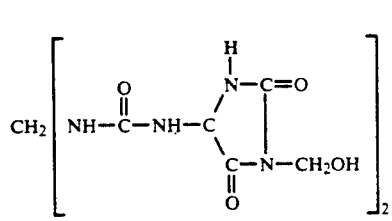

Imidiazolidinyl Urea

These most preferred compositions provide water based compositions that are so well stabilized that the risk of bacterial infection from their use are eliminated, essentially eliminated or substantially eliminated over extended periods of time, resulting in products that have a significant, as well as unpredictable, increase in shelf life or stability. These most preferred compositions allow the production of water based enzyme compositions that are stabilized against bacterial contamination and have a shelf life or stability of about two years or more. Moreover, such stabilized compositions are environmentally acceptable and safe to humans and animals who are exposed to or contact them.

Particular desirable compositions included amongst the most preferred compositions of the invention are those compositions containing a synergistic stabilizing amount of a. and sodium and/or potassium salt of benzoic acid and
b. diazolidinyl urea of the formula

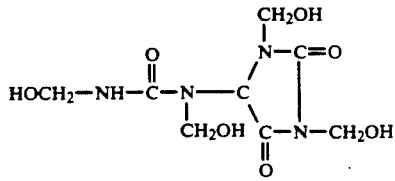

Diazolidinyl Urea and/or an imidazolidinyl urea of the formula

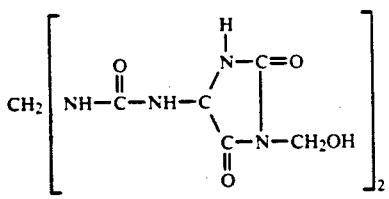

Imidiazolidinyl Urea

Mixed ureas and mixed salts are included within the scope of the invention. There are many instances where mixed alkali metal salts are more effective than one alkali metal salt and this invention contemplates the use of such mixed salts, especially those where the amount of one to the other is in the range of about one 1 gram atomic weight to about 10 gram atomic weight of one alkali metal to a gram atomic weight of the other metal. Particularly desirable would be a mixture of sodium and potassium.

The stabilization of such aqueous based compositions is much greater than is possible with either the salt of the carboxylic acid or the urea compound alone, that is, the use of both components results in a potentiation of the stabilization obtained. It has also been discovered that the use of such synergistic stabilizing amounts is especially effective in stabilizing water based enzyme compositions where, heretofore, the problems of instability due to bacterial contamination has been especially pronounced.

The stabilization of such aqueous based compositions, based on current evidence, is the most pronounced, within the scope of the invention, with the use of sodium and/or potassium benzoate and diazolidinyl urea and/or imidazolidinyl urea. In this case as well, but much greater than foreseeable, the use of sodium and/or potassium benzoate in combination with diazolidinyl urea and/or imidazolidinyl urea provides stabilization considerably superior to that obtainable from the use alone of sodium or potassium benzoate or diazolidinyl urea or imidazolidinyl urea. It has also been discovered that the use of such synergistic stabilizing amounts of sodium benzoate and diazolidinyl urea or imidazolidinyl urea is especially effective in stabilizing water based enzyme compositions where, heretofore, the problems of instability due to bacterial contamination has been especially pronounced.

The salt of the carboxylic acid and the urea compound, such as, sodium benzoate and diazolidinyl urea or imidazolidinyl urea stabilizers, can be added individually to the water based formulations in the appropriate amounts in order to obtain the desired stabilization. However, it is preferred that stabilizing compositions comprising mixtures of said two stabilizers be formed and that an appropriate effective stabilizing amount of a stabilizing composition be added to the water based systems.

The amounts of the salt of the carboxylic acid and the urea compounds are not narrowly critical. Typically, they may be used in a weight ratio of from about 0.1 to 10 of either the salt or the urea compound to the other. For example, where the stabilizing compositions comprise sodium benzoate and an effective bacterial stabilizing effective amount of diazolidinyl urea or imidazolidinyl urea, such stabilizing compositions will generally comprise sodium benzoate and diazolidinyl urea or imidazolidinyl urea in a weight ratio of from about 0.5:1 to about 1:0.5, most preferably in a weight ratio of about 1:1. The optimum stabilizing composition comprises a 1:1 mixture of sodium benzoate and diazolidinyl urea or imidazolidinyl urea.

The amount of such stabilizing composition added to water based compositions to stabilize such water based compositions against bacterial contamination will be any bacterial effective stabilizing amount, generally from about 0.05 to about 2%, preferably about 0.1 to about 1% and most preferably about 0.2 to about 0.5% weight percent of stabilizing composition based on the total weight of the water based composition. It will be appreciated that the amount of stabilizing composition incorporated in the water based compositions will vary with the type and components of the water based compositions.

The amount of each stabilizing component employed in the water based compositions to stabilize said compositions against bacterial contamination will generally be in an amount of from about 0.025% to about 1%, preferably about 0.05% to about 0.5% and most preferably from about 0.1% to about 0.25%, and most preferably about 0.1% by weight of each of the salt of the carboxylic acid, such as sodium benzoate, and the urea compounds, such as diazolidinyl urea or imidazolidinyl urea.

The unique synergistic antibacterial effective stabilizer combination of the salt of the carboxylic acid, e.g., sodium benzoate, and the urea compound, e.g., diazolidinyl urea or imidazolidinyl urea, may be employed to stabilize a wide variety of water based compositions where stabilization against bacterial contamination is a problem. As examples of such water based compositions in need of stabilization and which may be stabilized by the combination of stabilizers of this inventions, there may be mentioned, for example, the following type water based compositions: pharmaceuticals, cosmetics, odor and stain eradicators, ointments, bathing lotions, skin astringents, sunscreens, shampoos, hair treatment products such as hair conditions and permanent compositions, mousse removers, eye preparations, disinfectants, makeup removers, cleansing creams and lotions. The combination of stabilizers has been found to be particularly effective stabilizers for water based enzyme containing odor and stain eradicating compositions where stability of such compositions against bacterial contamination has been an especially prevalent need in order to increase the stability term or shelf life of such products.

The stabilizing compositions, the stabilized water based compositions and the process of stabilizing water based compositions against bacterial contamination is illustrated but not limited by the following examples.

EXAMPLE 1

A stabilizing composition of this invention comprises a 1:1 weight ratio mixture of sodium benzoate and diazolidinyl urea or imidazolidinyl urea. Other stabilizing compositions of this invention comprise the mixtures of sodium benzoate with diazolidinyl urea or imidazolidinyl urea in weight ratios of 0.5:1, 1:0.5, 0.75:1 and 1:0.75.

EXAMPLE 2

A commercially available enzyme containing water based product, VETCAIR ™, from Protech Inc., Stamford, Conn., was stabilized according to this invention and found to be stabilized against bacterial contamination in an unexpectedly superior synergistic manner from the combined use of sodium benzoate and imidazolidinyl urea compared to the use of either component alone. The VETCAIR TM product is an enzyme based product for neutralization or eradication of odors and prevention of stains due to animals such as dogs, cats, rabbits, ferrets, monkeys, horses and the like. The VETCAIR TM product is an enzyme containing water based product containing lyase, isomerase, ligase, oxidoreductase, transferase and hydrolase enzymes. Control A consisted of VETCAIR TM with no stabilizer added. Control B consisted of VETCAIR TM with 0.1% by weight sodium benzoate added and Control C consisted of VETCAIR TM with 0.1% imidazolidinyl urea added. For comparison purposes, two further control compositions were prepared, namely Control D consisting of VETCAIR TM with 0.1% propyl paraben added, Control E consisting of VETCAIR TM with 0.1% propyl paraben and 0.1% sodium benzoate.

A composition according to this invention was prepared and consisted of VETCAIR TM with 0.1% sodium benzoate and 0.1% imidazolidinyl urea added, designated Composition F.

All the compositions were tested for preservative or stabilization effectiveness according to the following two test procedures using two *Pseudomonas aeruginosa* product isolates identified as Q211-B and Q211-Y. Both cultures of the Pseudomonas product isolates were subcultured in Trypticase Soy Broth (TSB). The cultures were incubated for 24 hours at 30° C. One-tenth ml of 24 hour culture of each organism was used to challenge of the compositions.

The two test methods employed were as follows:

1. Challenge Test: The challenge test used was a modification of the Standard Cosmetic, Toiletries, and Fragrance Association Procedure. The products were challenged with the product isolates. Challenges were made with pure cultures. The challenge levels were $10^5$-$10^6$/ml. All product compositions were inoculated with 0.1 ml of inoculum and reinoculated with the same amount 7 days later. Aliquots of inoculated formulations were taken aseptically to allow determination of the number of microorganisms by a count of colonies after standing 4, 7, 14 and 28 days at 30° C.

2. Repeated inoculation-incubation test: Duplicate samples were prepared as described in the challenge test. Samples were restreaked on Trypticase Soy Agar (TSA) plus 1.5% Tween 80 after 24 hours incubation. The compositions samples and streak plates were then incubated at 30° C. Plates were read after 48 hours incubation. Samples were reinoculated after another 24 hours incubation at 30° C. (48 hours total incubation time between inoculations), and again streaked 24 hours later.

This procedure was repeated for a total of ten inoculation-incubation cycles. A stabilizer or preservative was considered to give adequate in-use protection only if it maintained sterility in the test sample throughout all ten inoculation-incubation cycles.

To quantitatively determine the stabilization effectiveness serial tenfold dilutions of challenged compositions from $10^{-1}$-$10^{-6}$ were made in phosphate buffer; 0.1 ml aliquots were removed from each dilution and placed on the surface of the TSA+Tween 80 plate. A sterile glass rod was used to streak the sample uniformly over the plate. Counts were made and recorded as colony forming unit (CFU)/ml.

The results of the bacterial challenge test (Test 1) are set forth in Table 1.

TABLE 1

| | *P. aeruginosa* Q211-B Days after | | | CFU/ml | *P. aeruginosa* Q211-Y Days after | | | |
|---|---|---|---|---|---|---|---|---|
| COMPOSITION | 4 | 7 | 14 | 28 | 4 | 7 | 14 | 28 |
| Control A | <10 | $2 \times 10^5$ | $4.2 \times 10^6$ | $1.3 \times 10^8$ | — | — | — | — |
| Control B | <10 | $2.5 \times 10^5$ | $3.5 \times 10^6$ | $7.0 \times 10^7$ | — | — | — | — |
| Control C | <10 | <10 | <10 | <10 | <10 | <10 | $3 \times 10^5$ | $2 \times 10^5$ |
| Control D | <10 | <10 | $2 \times 10^6$ | $1.8 \times 10^6$ | <10 | <10 | $5 \times 10^4$ | $2.5 \times 10^6$ |
| Control E | <10 | $9.8 \times 10^4$ | $3.9 \times 10^6$ | $2.6 \times 10^7$ | <10 | <10 | $2 \times 10^5$ | $1.6 \times 10^7$ |
| Control F | <10 | <10 | <10 | <10 | <10 | <10 | <10 | <10 |

All samples were reinoculated with 0.1 ml of inoculum at day 7.
Numbers represent colony forming unit/ml (CFU/ml).

The test results of the challenge test in Table 1 indicate that only Composition F containing both sodium benzoate and imidazolidinyl urea exhibited effective bacterial contamination control by rapidly reducing and essentially eliminating the contaminating bacterial inoculums in the products.

Test 2, the repeated inoculation-incubation test, is a test indicative of the product composition maintaining control of microorganisms during repeated or constant use. The results of this test are set forth in Table 2.

TABLE 2

| Day | A | B | C | D | E | F |
|---|---|---|---|---|---|---|
| 1 | — | + | — | — | — | — |
| 3 | + | + | — | — | — | — |
| 5 | + | + | — | — | — | — |
| 7 | + | ++ | — | + | + | — |
| 9 | ++ | ++ | + | + | + | — |
| 11 | +++ | +++ | + | + | +++ | — |
| 15 | +++ | +++ | + | ++ | +++ | — |
| 28 | +++ | +++ | ++ | +++ | +++ | — |

— No growth
+ Slight growth
++ Moderate growth
+++ Heavy growth

The results of this repeated insult test indicate that of the tested compositions only Composition F provides effective protection to control growth of *P. aeruginosa* microoganisms during constant use.

Substitution of diazolidinyl urea in place of imidazolidinyl was in Compositions C and F in each of the aforesaid challenge tests and repeated inoculation-incubation tests produce similar stabilization results.

In addition to stabilizing and preserving water based compositions against growth of *P. aeruginosa* as set forth hereinbefore, the stabilizer compositions of this invention have also been shown to be effective stabilizing and preserving water based compositions against the following organisms: *Staphylococcus aureus, Escherichia coli, Aspergillus niger, Candida albicans* and *Bacillus cereus.*

The combination of sodium benzoate and diazolidinyl urea not only synergistically protects water based compositions against microbial contamination, but is considered environmentally acceptable and safe to humans and animals.

Though this invention has been described in the examples with respect to specific materials, it is not intended that the invention be limited thereto. The invention contemplates the use of a variety of materials encompassed by the description herein set forth.

We claim:

1. A stabilizer composition for protecting aqueous based compositions against microbial growth comprising sodium benzoate and a stabilizing effective amount of a urea compound selected from the group consisting of diazolidinyl urea and imidazolidinyl urea.

2. A stabilizer composition of claim 1 comprising sodium benzoate and the urea compound in a weight ratio of from about 0.5:1 to about 1:05.

3. A stabilizer composition of claim 1 comprising sodium benzoate and the urea compound in a weight ratio of about 1:1.

4. An aqueous based composition stabilized against microbial growth comprising an aqueous based composition selected from the group consisting of pharmaceuticals, cosmetics, odor and stain eradicators, bathing lotions, skin astringents, sunscreens, shampoos, hair treatment products, mousse removers, eye preparations, disinfectants, makeup removers and cleansing creams or lotions, and a stabilizing effective amount of sodium benzoate and a urea compound selected from the group consisting of diazolidinyl urea and imidazolidinyl urea.

5. An aqueous based composition of claim 4 wherein the amount of sodium benzoate present is from about 0.05% to about 0.5% by weight and the amount of the urea compound present is from about 0.05% to about 0.5%.

6. An aqueous based composition of claim 5 wherein the sodium benzoate and the urea compound are each present in an amount of about 0.1% by weight.

7. An aqueous based composition of claim 4 wherein the aqueous based composition is an enzyme containing aqueous based composition.

8. An aqueous based composition of claim 5 wherein the aqueous based composition is an enzyme containing aqueous based composition.

9. An aqueous based composition of claim 6 wherein the aqueous based composition is an enzyme containing aqueous based composition.

10. An aqueous based composition of claim 7 wherein the enzyme containing aqueous based composition is an odor or stain eradicator containing a mixture of lyase, isomerase, ligase, oxidoreductase, transferase and hydrolase enzymes.

11. An aqueous based composition of claim 8 wherein the enzyme containing aqueous based composition is an odor or stain eradicator containing a mixture of lyase, isomerase, ligase, oxidoreductase, transferase and hydrolase enzymes.

12. An aqueous based composition of claim 9 wherein the enzyme containing aqueous based composition is an odor or stain eradicator containing a mixture of lyase, isomerase, ligase, oxidoreductase, transferase and hydrolase enzymes.

13. An aqueous composition suitable for providing improved stability with respect to bacterial contamination comprising synergistically stabilizing amounts of sodium benzoate and a urea compound selected from the group consisting of diazolidinyl urea and imidazolidinyl urea.

* * * * *